United States Patent [19]

Nodai et al.

[11] 4,453,917

[45] Jun. 12, 1984

[54] FACE BOW

[75] Inventors: Etsuo Nodai, Fukuoka; Takeshi Watanabe, Fukushima, both of Japan

[73] Assignee: GAC International, Inc., Commack, N.Y.

[21] Appl. No.: 489,580

[22] Filed: Apr. 28, 1983

[51] Int. Cl.³ .............................................. A61C 7/00
[52] U.S. Cl. ...................................................... 433/5
[58] Field of Search ........................................... 433/5

[56] References Cited

U.S. PATENT DOCUMENTS

| | | | |
|---|---|---|---|
| 664,412 | 12/1900 | Knapp | 433/5 |
| 3,866,322 | 2/1975 | Broussard | 433/5 |
| 3,997,971 | 12/1976 | Moss | 433/5 |
| 4,087,915 | 5/1978 | Andrews | 433/5 |
| 4,212,637 | 7/1980 | Dougherty et al. | |

Primary Examiner—Robert Peshock
Attorney, Agent, or Firm—Kenyon & Kenyon

[57] ABSTRACT

An improved orthodontic face bow is disclosed. The face bow includes first and second bow-shaped members. The first bow-shaped member is worn inside the mouth and has means for attachment to the teeth to be displaced distally. The second bow-shaped member is worn extra-orally and has means for attachment to a tension-applying means such as an elastic strap worn around the neck or head. The first and second bow-shaped members have means for removably coupling the two bow-shaped members together. This feature allows the second outer bow-shaped member to be uncoupled from the first bow-shaped member without removing the first inner bow-shaped member from the mouth, thus making the face bow much safer than known face bows of one piece construction.

3 Claims, 10 Drawing Figures

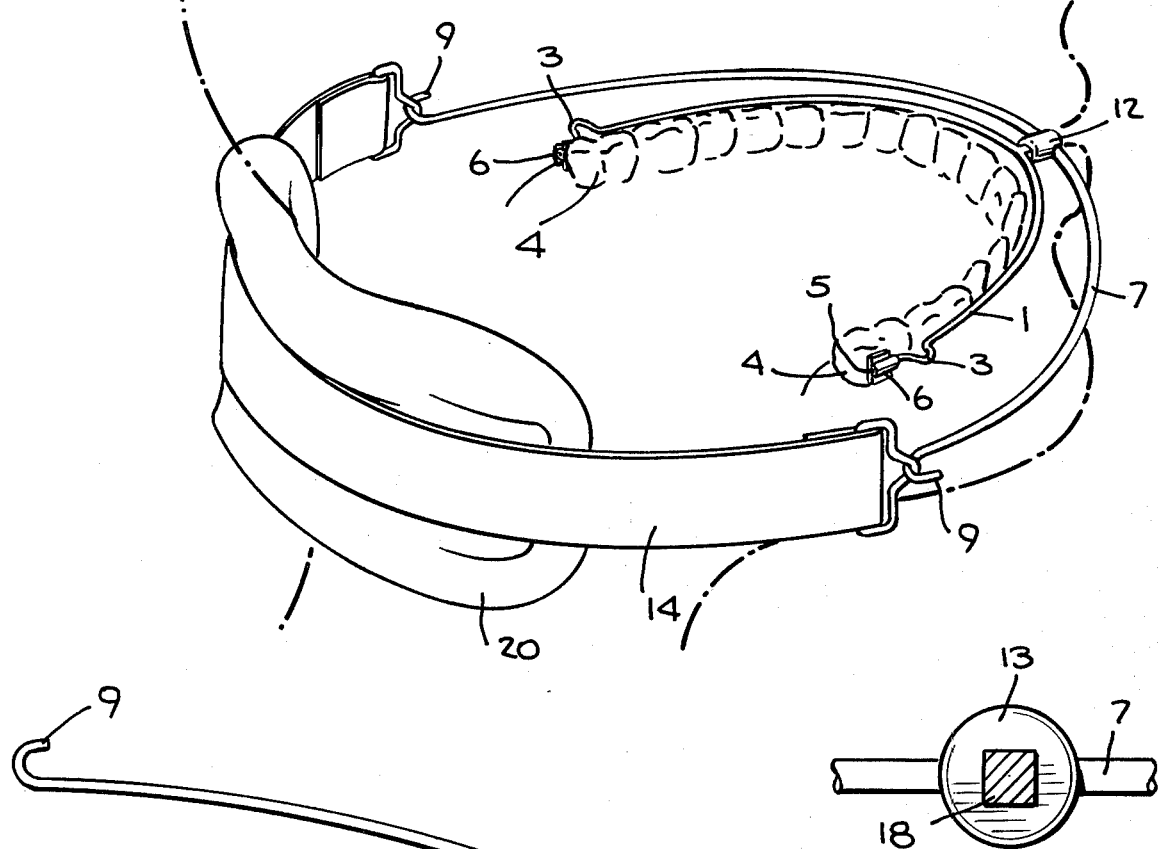
Fig. 1.
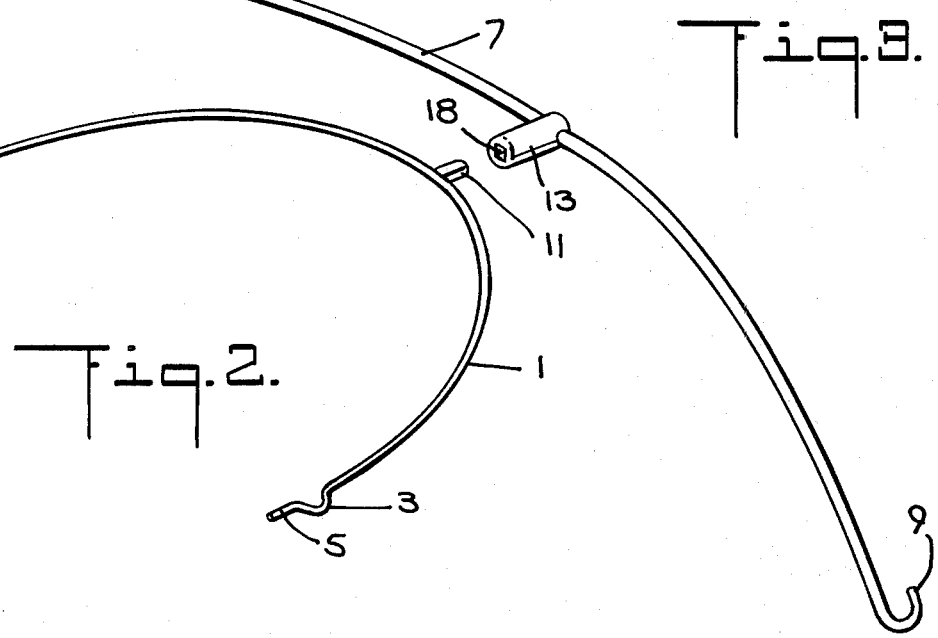
Fig. 2.
Fig. 3.

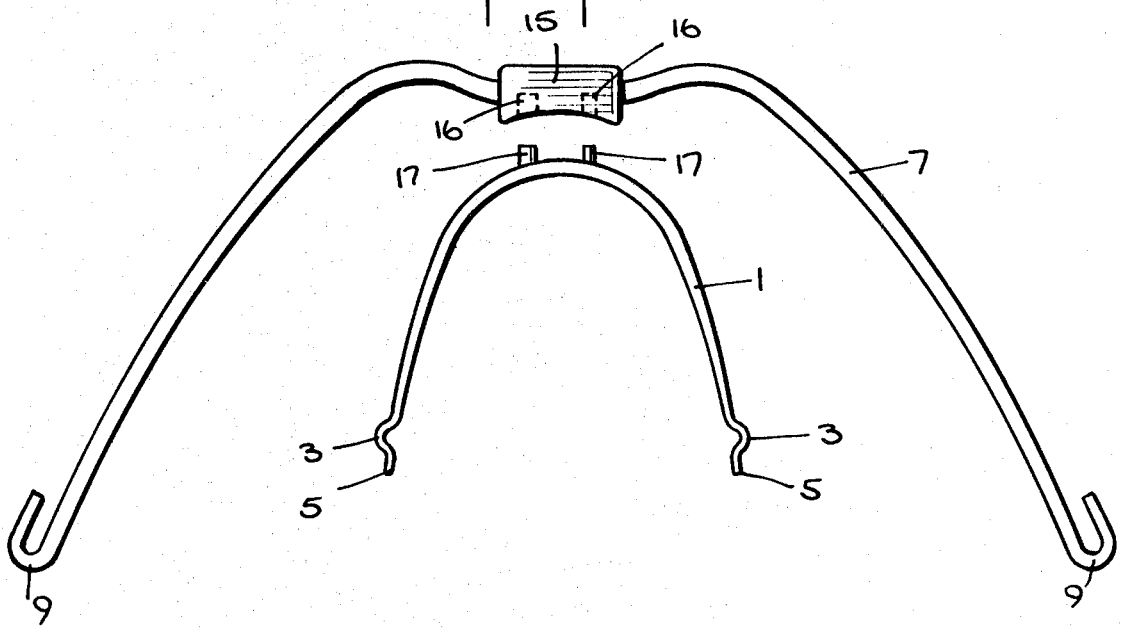
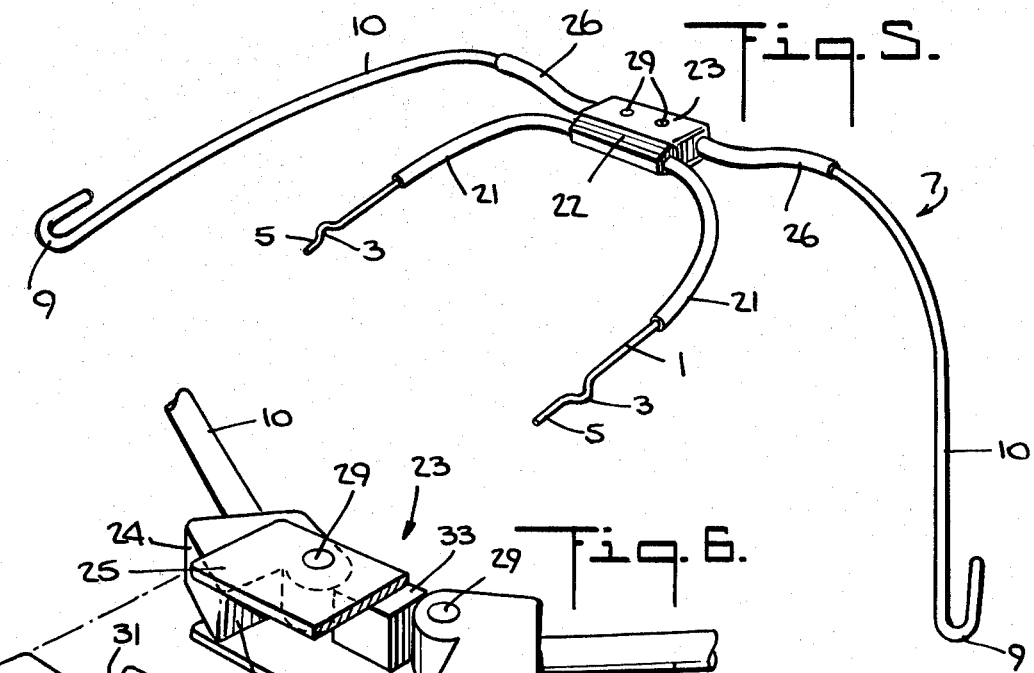
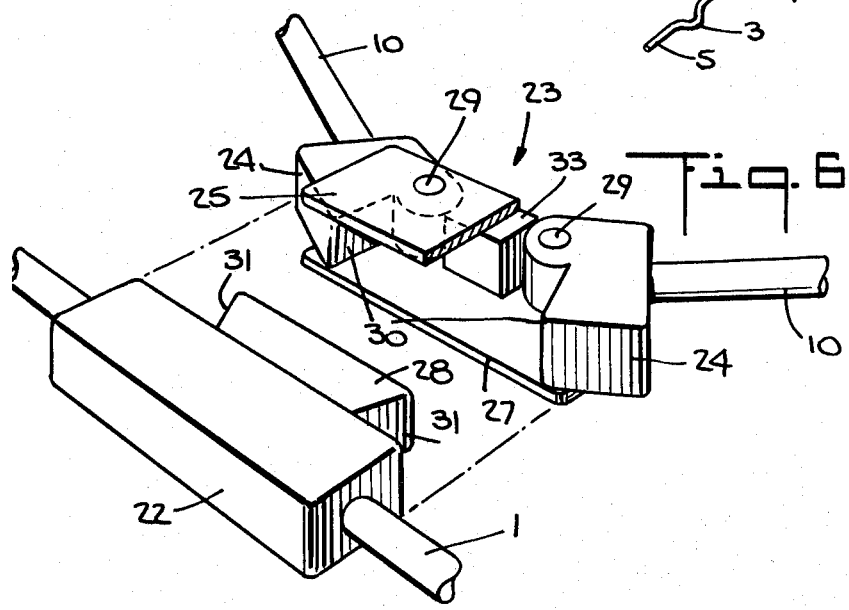

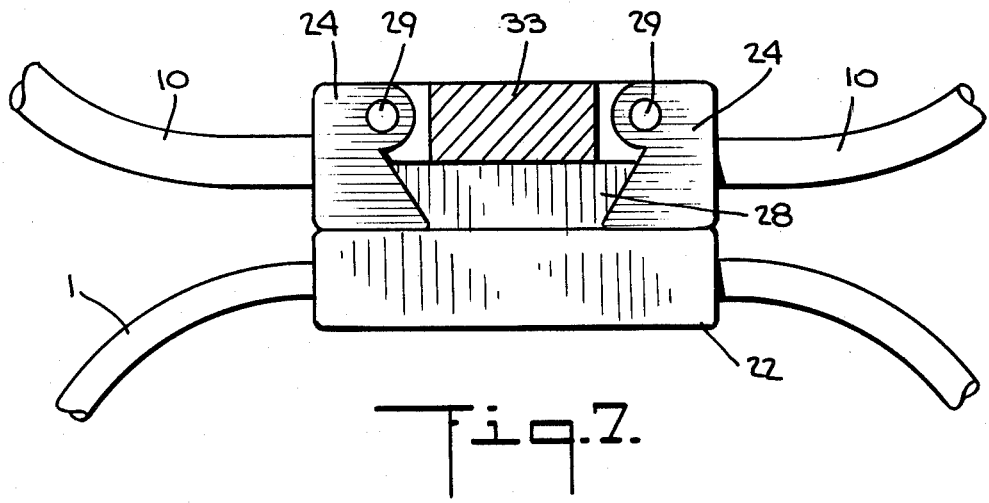
Fig. 7.
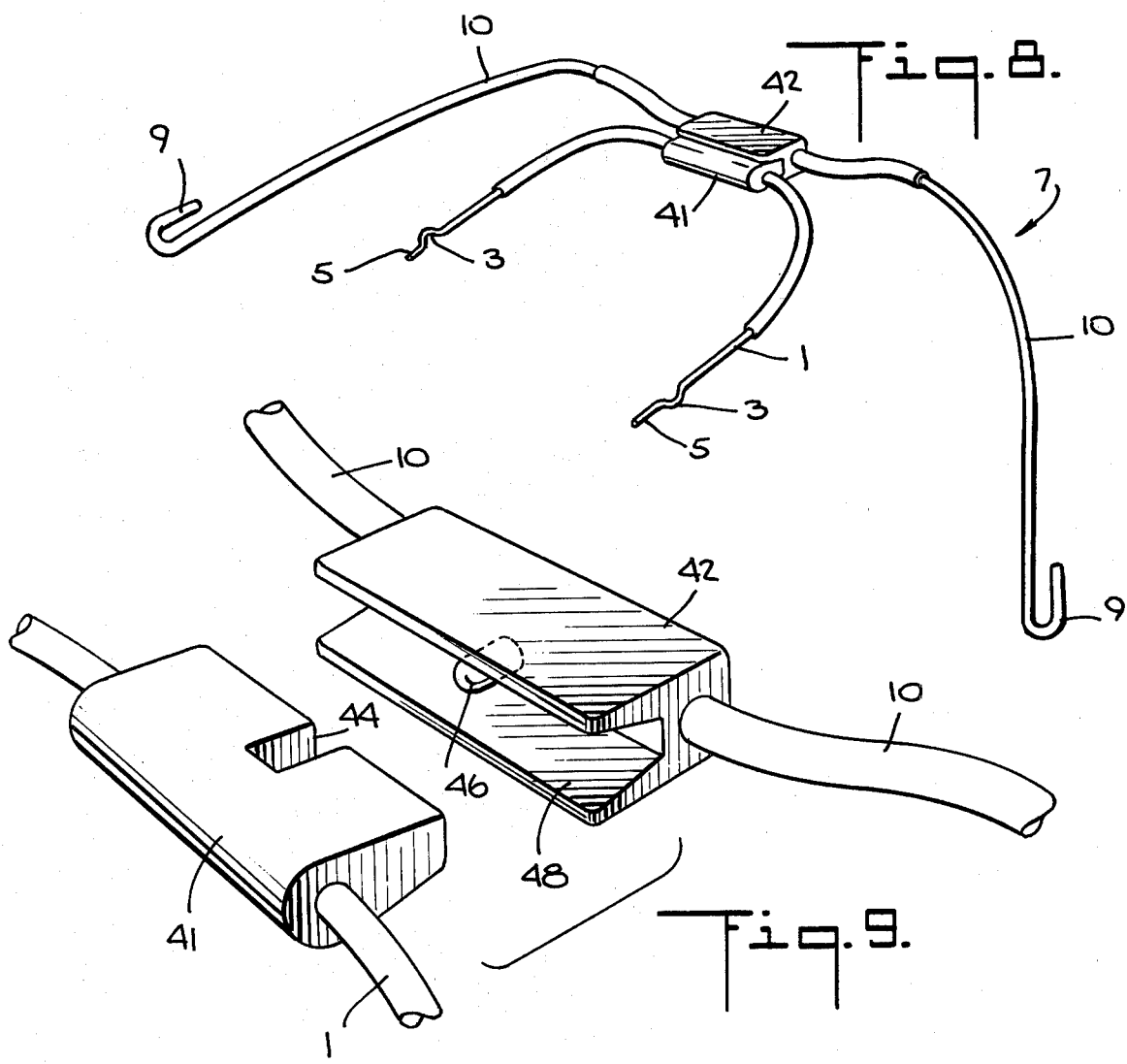
Fig. 8.
Fig. 9.

FACE BOW

BACKGROUND OF THE INVENTION

The present invention relates to orthodontic devices, and more particularly to face bows.

Face bows are utilized in the orthodontic practice generally to gradually drive molar teeth distally and to correct molar protrusions and irregularities and relieve overcrowding of the molar teeth. Quite basically, a face bow comprises an orthodontic device which includes an orally worn inner bow-shaped element designed in accordance with the curvature of the denture. At substantially the outer concave center of the inner bow, an outer extra-oral bow is permanently physically attached to the inner bow. The outer bow is generally longer than the inner bow and has greater radii of curvature. The inner bow is worn along the inside of the mouth and generally is attached to the teeth by means of tubular brackets, known as buccal tubes, mounted to the molar teeth to be moved. Stops, loops or offsets on the inner bow transmit a force to the molar teeth and control the amount of distal movement provided by the face bow. The ends of the outer bow are generally attached to an elastic neck strap or headgear which is worn around the back of the neck or head, depending on the direction of force to be applied. The tension provided by the elastic neck strap or headgear serves to put constant pressure on the teeth to which the inner bow is attached, causing the molars to be moved distally with respect to the anterior teeth and the center of the mouth, thus allowing space for rearward movement of the more anterior teeth.

The use of face bows in the orthodontic art is well known. Face bows do, however, have certain disadvantages. They must be worn for extended periods of time to have an effect and the most likely users are children. The danger thus exists that the face bow might be pulled out of the user's mouth either deliberately or accidentally, while at play, etc. There is thus a danger that the sharp ends and hooks, particularly of the inner bow, might come in contact with the user's skin or eyes, possibly causing lacerations or blindness. There have been several known cases of blindness caused by face bows.

Several devices exist which attempt to solve this safety problem, but they all involve the neck strap or headgear providing for disengagement after the face bow has been moved forward a certain distance. The disadvantage of this type of device is that it might fail to provide sufficient force to move the teeth if not properly adjusted. Another known device uses a hook requiring a rearward movement of the inner bow before disengagement from the teeth. This device makes it more difficult to remove from the mouth, even under normal circumstances, and could result in excessive forces being applied to the teeth should the face bow be accidentally pulled outward.

Accordingly, it is an object of the present invention to provide a face bow which is safe and eliminates the above dangers of the known face bows.

It is a further object of the present invention to provide a face bow having an inner bow which can be permanently wired to the teeth and yet which allows easy removal of the outer bow prior to or during normal activities, such as eating.

It is yet a further object of the present invention to provide a face bow wherein different outer bows can be used with the same inner bow, which may be permanently wired to the teeth.

Conversely, it is an object of the present invention to provide a face bow wherein more than one type of inner bow can be used with the same outer bow.

Furthermore, it is an object of the present invention to provide a face bow which allows the same outer bow to be used with a different inner bow so that when the inner bow requires changing due to growth, breakage or the chemical stress of the oral environment, the same outer bow can be reused, thus extending the life of the outer bow and eliminating some expense.

Furthermore, it is an object of the present invention to provide a face bow which can be easily inserted into the mouth by the user.

SUMMARY OF THE INVENTION

These and other objects of the present invention are achieved by a face bow comprising: a first bow-shaped member having means at the ends thereof for fastening to teeth to be moved in the mouth of a user; a second bow-shaped member having means at the ends thereof for attaching to a tension-applying means; and means for removably coupling the first and second bow-shaped members to each other so that when the second bow-shaped member is pulled away from the first bow-shaped member, the two bow-shaped members separate.

Various embodiments of the invention will be described in more detail below.

BRIEF DESCRIPTION OF THE DRAWINGS

The present invention will be described in greater detail in the following detailed description with reference to the drawings, in which:

FIG. 1 shows in phantom perspective view generally how a face bow may be worn by a user and illustrates a first embodiment of the invention having means for removably coupling the inner and outer bows;

FIG. 2 is an exploded perspective view of the embodiment shown in FIG. 1;

FIG. 3 is a cross sectional view through the coupling means of the embodiment shown in FIGS. 1 and 2;

FIG. 4 is an exploded top view of a second embodiment of the invention;

FIG. 5 is a perspective view of a third embodiment of the invention;

FIG. 6 is an exploded perspective view of details of the coupling means of the embodiment shown in FIG. 5;

FIG. 7 is a top sectional view of the coupling means shown in FIG. 6;

FIG. 8 is a perspective view of a fourth embodiment of the invention;

FIG. 9 is an exploded view of details of the coupling means of the embodiment shown in FIG. 8.

DETAILED DESCRIPTION

Figure 10:
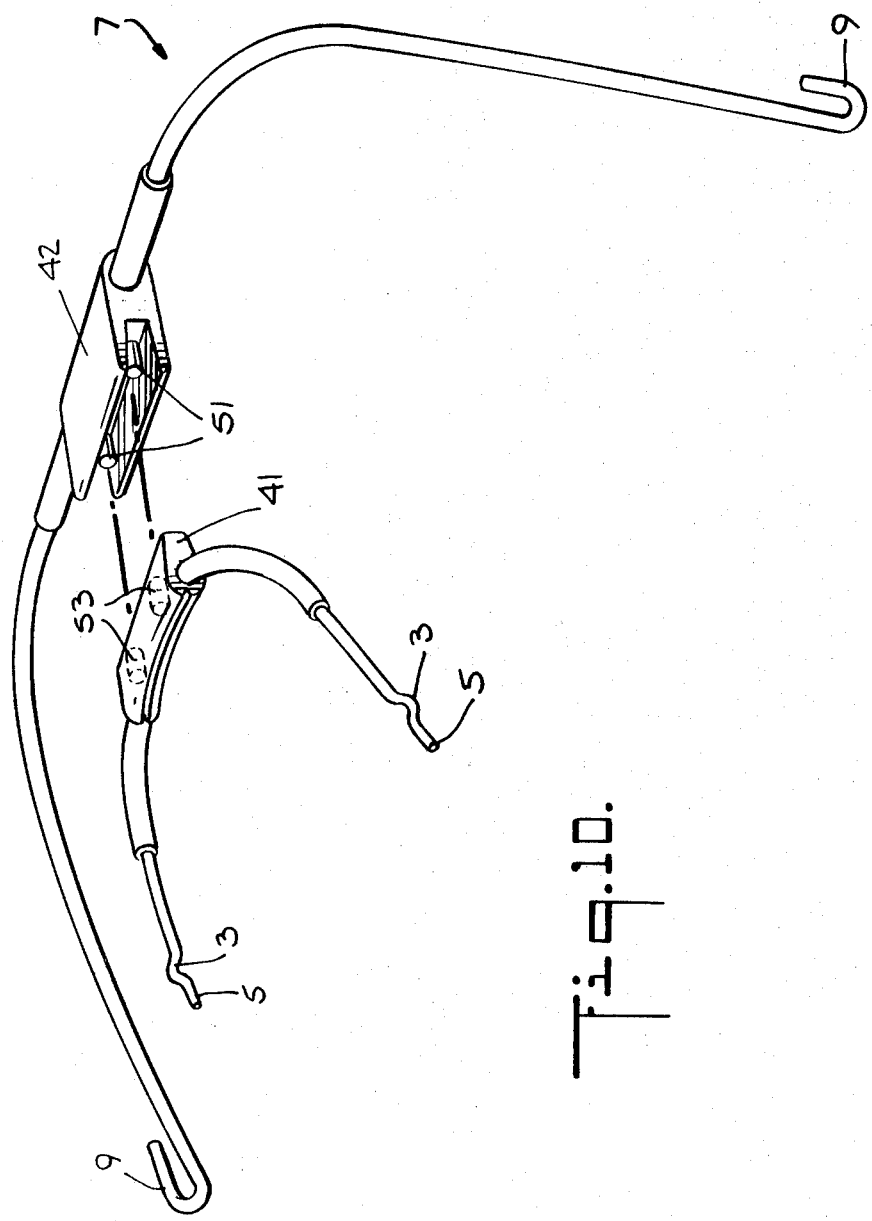
FIG. 10 is an exploded view of details of a fifth embodiment of the invention.

With reference now to the drawings in which like members are numbered with like reference numerals, FIG. 1 shows generally how a face bow according to the invention may be worn by a user. FIGS. 2 and 3 illustrate in more detail the embodiment shown in FIG. 1. The improved face bow comprises an inner bow 1 having loops or offsets 3 for limiting the distal movement of the molar teeth 4 to which the inner bow is attached. The ends 5 of the inner bow 1 fit into corresponding tubular brackets or buccal tubes 6 which are wired or bonded to the teeth to be moved. The inner bow 1 has an arch which conforms to the denture or dental pattern of the human mouth. The face bow further comprises an outer bow 7 having hook-shaped ends 9, to which the elastic headgear or neck strap 14 is attached and which provides tension on the outer bow 7, which tension is transmitted to the inner bow 1, thus causing gradual distal movement of the teeth to which the inner bow is attached. A protective pad 20 cushions the back of the neck of the face bow user. A means for removably coupling the inner bow 1 to the outer bow 7 is shown by reference numeral 12. In the embodiment shown in FIGS. 1 to 3, the means for removably coupling comprises a projection 11 on the inner bow 1 which fits into a corresponding apertured receptacle 13 on the outer bow 7. The projection may be round in cross section, but is preferably of some other keyed cross section, such as a square, as shown, or a triangle, so that rotation of the outer bow in the plane parallel to the face of a user is prevented. The corresponding aperture 18 of receptacle 13 into which projection 11 fits is shown more clearly in cross section in FIG. 3. Receptacle 13 is preferably rounded on its outer surfaces so that injury to the user's face or eyes is prevented when the outer bow is separated from the inner bow. Although not essential because the tension due to the elastic neck strap or headgear will maintain the outer bow in position on the inner bow, the projection 11 and receptacle 13 can be made so as to provide a snap fit. This might be especially useful in applications wherein the inner bow 1 is permanently wired to the teeth.

FIG. 4 illustrates a second embodiment of the invention. Instead of a single projection 11 and apertured receptacle 13 as shown in FIG. 1, the embodiment of FIG. 4 includes two projections 17 which fit into two apertures 16 of member 15 connecting the left and right arms of the outer bow 7. Outer bow 7 and member 15 may be a one piece integral unit or may be made in multiple sections which are attached together by suitable means, such as by welding. Preferably, the two projections are of different cross sections or cross sectional areas as shown so that outer bow 7 can be attached in only one way to the inner bow 1. This is particularly significant if the left and right molars to which the inner bow is attached must be moved different amounts and the outer bow 7 therefore has left and right arms of unequal length so that unequal tension is applied to the left and right molars. Additionally, more than two projections could also be used.

FIGS. 5, 6 and 7 show a third embodiment of the invention. The means for coupling the inner and outer bows comprises a member 22 attached to the inner bow 1 and a member 23 attached to outer bow 7. Member 22 may have a trapezoidally shaped projection 28 and may connect the two arms of the inner bow 1. Again, the inner bow 1 can be a one piece integral unit or can be made from the appropriate sections coupled together by suitable means. In this embodiment, both the inner bow 1 and outer bow 7 have protective plastic sheaths, 21 and 26 respectively, covering the arms of the inner and outer bows. The outer bow 7 has two arms 10. Each of the arms 10 is connected to a pivoting member 24. The pivoting members 24 are mounted on pivot pins 29 between two plates 25 and 27, plate 25 being shown sectioned so as to reveal the pivoting members 24. The pivoting members 24 have internal surfaces 30 which engage with the sloping sides 31 of trapezoidal projection 28. Plates 25 and 27 and pivoting members 24 may be provided with appropriate detent or locking means so that the outer bow sufficiently locks to the inner bow, yet the two may be disconnected by appropriately flexing the outer bow. Detents are not necessary however, because the tension provided by the elastic neck strap or headgear on the outer bow will keep it securely coupled to the inner bow. A block member 33 is provided between the plates 25 and 27 and limits the travel of projection 28 into the aperture between members 24.

Additionally, the face bow shown in FIGS. 5, 6 and 7 could be modified so that one arm 10 is fixedly mounted to the plates 25 and 27 and only the other arm 10 is pivotally mounted on a pivot pin. In this embodiment, the side 31 of projection 28 facing the fixed arm preferably would be made at a right angle to the longitudinal direction of member 22 instead of being angled as shown so that the outer bow will readily retract from the inner bow if an outward force is applied to the fixed arm.

FIGS. 8 and 9 illustrate a fourth embodiment of the invention. Inner bow 1 and outer bow 7 are connected together by members 41 and 42. Member 41 comprises a substantially rectangular connecting member for the two arms of the inner bow 1 if the inner bow has separate arms or may be made integral with the two arms if the inner bow is a one piece unit. Member 41 further includes aperture 44. Member 42 comprises a connecting member for the two arms 10 of the outer bow 7 if the outer bow is made from separate sections or may be made integral with the two arms 10 if the outer bow is a one piece unit, and includes a generally truncated v-shaped channel 48 into which the substantially rectangular truncated v-shaped member 41 fits. A projection 46, which can be round or of some other keyed cross section (especially where the left and right arms 10 are of different lengths), fits into aperture 44, which may be appropriately shaped. Thus, like the other embodiments described herein, the outer bow is securely fastened to the inner bow, while at the same time the outer bow may be easily separated from the inner bow and the outer bow is prevented from rotating on the inner bow. Again, it must be noted that the inner and outer bow and the respective connecting members 41 and 42 may be one piece integral units.

FIG. 10 is a perspective view of a fifth embodiment of the invention. This embodiment is similar to the embodiment shown in FIGS. 8 and 9 but includes two projections 51 which mate with corresponding apertures in member 41. More than two projections could also be used and the projections can be of unequal size so that the outer bow can be assembled to the inner bow in only one way. This embodiment helps in controlling any tendency of the outer bow to rock in the plane parallel to the outer bow.

The described face bow has many advantages over the known face bows. In addition to safety considerations, the face bow allows the outer bow to be easily removed or installed by the user. If the inner bow is permanently installed on the teeth, the outer bow can be conveniently installed by the user to the inner bow without having to be slipped into the buccal tubes attached to the teeth, which can be an awkward operation, especially for children. If the inner bow is not permanently installed, the inner bow can be more easily installed into its tooth mounted brackets or buccal tubes without the bulky and awkward outer bow being coupled thereto. Different inner and outer bow combinations can be used, thus making the face bow according to the invention more versatile than known face bows. The same outer bow can be used with different inner bows, which are more often replaced due to dental growth or breakage, which often occurs to inner bows as a result of adjustment by dental personnel. Thus, the present invention eliminates the expense of having to replace the entire face bow.

Further modifications of the invention are also possible. For example, the various projections and apertured receptacles of the different described embodiments could be reversed so that the projection is attached to the outer bow 7 and the receptacle is attached to the inner bow 1. Of course, the projection on the outer bow must be made so that no sharp edges can come into contact with a user's eyes or face.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. A facebow comprising:
    a first bow-shaped member having means at the ends thereof for fastening to teeth to be moved in the mouth of a user;
    a second bow-shaped member having means at the ends thereof for attaching to a tension-applying means, said second bow-shaped member including left and right arms forming said bow-shaped member; and
    means for removably coupling said first and second bow-shaped members to each other so that when said second bow-shaped member is pulled away from said first bow-shaped member, said two bow-shaped members separate, said means for coupling further comprising:
    a projection disposed on said first bow-shaped member so as to be substantially near the center of the mouth when the face bow is installed in the mouth of a user;
    first and second plate means disposed in adjacent parallel relationship;
    first pivot means connecting said first and second plate means; and
    first means pivotally mounted on said pivot means and attached to one of said arms, said pivotally mounted means being spaced apart from the other of said arms so as to form an aperture therebetween for receiving said projection, said pivotally mounted means including a surface which engages with a surface of said projection so that when said arm attached to said pivotally mounted means is pivoted toward said first bow-shaped member and said projection is disposed in said aperture, said second bow-shaped member is locked to said first bow-shaped member and when at least one of said arms is pivoted away from said first bow-shaped member said two bow-shaped members may be separated.

2. The face bow recited in claim 1, further comprising:
    second pivot means disposed between said first and second plate means opposite said first pivot means; and
    second means pivotally mounted on said second pivot means and attached to the other of said arms, said first and second pivotally mounted means being spaced apart from each other so as to form an aperture therebetween for receiving said projection, said first and second pivotally mounted means each including a surface which engages with respective surfaces of said projection so that when at least one of said arms is pivoted toward said first bow-shaped member and said projection is disposed in said aperture, said second bow-shaped member is locked to said first bow-shaped member and when at least one of said arms is pivoted away from said first bow-shaped member, said two bow-shaped members may be separated.

3. The face bow recited in claim 2 wherein said projection has a trapezoidal shape having angled sides wherein the width of said projection increases progressively in the direction away from said first bow-shaped member, the angled sides of said projection forming the surfaces which engage with surfaces of said pivotally mounted means, the surfaces of said pivotally mounted means shaped so as to conform to said angled sides.

* * * * *